United States Patent [19]
Klimov et al.

[11] Patent Number: 5,770,458
[45] Date of Patent: Jun. 23, 1998

[54] APPARATUS AND METHOD FOR CONDUCTING A BINDING ASSAY ON AN ABSORBANT CARRIER MATERIAL

[75] Inventors: Alexei Dmitri Klimov, Princeton; Shiow-Chuan Jane Tsai, Flemington, both of N.J.

[73] Assignee: Roche Diagnostics Systems, Inc., Branchburg, N.J.

[21] Appl. No.: 877,189

[22] Filed: Jun. 17, 1997

Related U.S. Application Data

[63] Continuation of Ser. No. 385,300, Feb. 10, 1995, abandoned.

[51] Int. Cl.[6] .................................................. G01N 33/543
[52] U.S. Cl. ....................... 436/518; 436/524; 436/538; 436/810; 435/7.1; 435/7.2; 435/174; 435/970; 435/971; 422/56; 422/58; 422/104; 422/110
[58] Field of Search .............................. 422/56, 58, 187, 422/188, 104, 110, 278; 435/7.1, 7.2, 7.8, 7.92, 7.94, 7.95, 174, 970, 971, 7.93; 436/518, 524, 538, 530, 535, 533, 810

[56] References Cited

U.S. PATENT DOCUMENTS

| | | |
|---|---|---|
| 3,857,931 | 12/1974 | Hager . |
| 4,094,647 | 6/1978 | Deutsch et al. . |
| 4,121,975 | 10/1978 | Ullman et al. . |
| 4,235,601 | 11/1980 | Deutsch et al. . |
| 4,361,537 | 11/1982 | Deutsch et al. . |
| 4,599,327 | 7/1986 | Nògràdi et al. . |
| 4,798,804 | 1/1989 | Khanna et al. . |
| 4,837,168 | 6/1989 | de Jaeger et al. . |
| 4,861,711 | 8/1989 | Friesen et al. ............................. 436/7 |
| 4,938,927 | 7/1990 | Kelton et al. . |
| 4,956,302 | 9/1990 | Gordon et al. . |
| 5,126,333 | 6/1992 | Martini et al. . |
| 5,238,652 | 8/1993 | Sun et al. . |
| 5,275,785 | 1/1994 | May et al. . |
| 5,403,551 | 4/1995 | Galloway et al. . |
| 5,411,893 | 5/1995 | Eden et al. . |

FOREIGN PATENT DOCUMENTS

| | | |
|---|---|---|
| 271 854 | 6/1988 | European Pat. Off. . |
| 353 500 | 2/1990 | European Pat. Off. . |
| 386 644 | 9/1990 | European Pat. Off. . |
| 560 410A2 | 1/1993 | European Pat. Off. . |
| 525 829 | 2/1993 | European Pat. Off. . |
| 560 411 | 9/1993 | European Pat. Off. . |
| 291 194B1 | 2/1994 | European Pat. Off. . |
| 87/02774 | 5/1987 | WIPO . |
| 92/01226 | 1/1992 | WIPO . |
| 95/07659 | 3/1995 | WIPO . |

OTHER PUBLICATIONS

Derwent Abstract No. AN–88–169148.
Derwent Abstract No. AN–90–037898.
Derwebt Abstract No. An–90–194332.
Birnbaum, S., *Anal. Biochem.*, 206:168–171 (1992).
Burkert, W.G., et al., *J. Liquid Chromatogr.*, 4:1065–1085 (1981).
Croft, A.P., et al., *Tetrahedron*, 39(9):1417–1474 (1993).
Cserhati, T., et al., *J. Chromatogr.*, 259:107–110 (1983).
Cserhati, T., et al., *J. Inclusion Phenom.*, 1:53–59 (1983).
Cserhati, T., et al., *J. Inclusion Phenom.*, 1:395–402 (1983).
Cserhati, T., et al., *J. Inclusion Phenom.*, 4:55–59 (1986).
Duchene, D., et al., *J. Coord. Chem.*, 27:223–236 (1992).
Galloway, R., *Seradyn, Inc.*, pp. 6–31 (1988).

(List continued on next page.)

*Primary Examiner*—James C. Housel
*Assistant Examiner*—Bao-Thuy L. Nguyen
*Attorney, Agent, or Firm*—George W. Johnston; William H. Epstein; John P. Parise

[57] ABSTRACT

Binding assays are effected by introducing a specific binding reagent through a top absorbant membrane in parallel contact with a main absorbant membrane. By providing a parallel flow of liquid in the two membranes, and by controlling the flow of the diluted reagent from the top absorbant membrane into the main absorbant membrane, a controlled, uniform dilution of the reagent is obtained, leading to more accurate assay results.

19 Claims, 4 Drawing Sheets

OTHER PUBLICATIONS

Harvey, *Schleicher & Schuell,* No. 557, pp. 18–31 (1991).

Horton, J.K., et al., *J. Immunol. Methods,* 140:131–134 (1991).

Illum, L., et al., *Methods in Enzymology,* 112:67–84 (1985).

Schwartz, A., et al., *J. Org. Chem.,* 51:5463–5465 (1986).

Sybilskia, D., et al., Inclusion Compounds, V. 3, Ed. J.L. Atwood, et al., Academic Press, pp. 208–243 (1984).

Sybilska, D., et al., Ordered Media in Chemical Separations, ed.

W.L. Hinze, et al., ACS Symposium Series 342, American Chemical Society, Washington, DC, pp. 218–234 (1987).

Szejtli, J., et al., Ordered Media in Chemical Separations, Ed. W.L. Hinze, et al., ACS Symposium Series 342, American Chemical Society, Washington, DC, pp. 200–217 (1987).

Szejtili, J., et al., Inclusion Compounds, V. 3, Ed. J.L. Atwood, et al., Academic Press, pp. 331–390 (1984).

Derwent Abstract No. AN 93–283006/36 of J 5–196623.

APPARATUS AND METHOD FOR CONDUCTING A BINDING ASSAY ON AN ABSORBANT CARRIER MATERIAL

This is a continuation of application Ser. No. 08/385,300, filed Feb. 10, 1995, now abandoned.

BACKGROUND OF THE INVENTION

1. Field

The present invention relates generally to methods and devices to carry out binding assays, and specifically to assays which utilize porous carrier materials for transporting reagents.

2. Description

Specific binding assays are valuable tools useful in numerous applications. Such assays involve two or more binding components, one of which is analyte. Examples of specific binding components include antibody and antigen, DNA and/or RNA hybridization, and receptor-ligand interaction. Numerous specific binding assays formats are known in the art, and include competition, sandwich, and agglutination assays. Unfortunately, specific binding is not always observable. Accordingly, labeling techniques have been developed to make the binding either indirectly or directly observable. Labeling typically involves attaching a detectable label to one or both binding components.

Radioisotopes, fluorophores, and enzymes are examples of "indirect" labels, since they require instrumentation and/or special treatment for detection. In contrast, "direct" labels are visible to the naked eye and do not require special procedures or instrumentation for detection. Metallic sols, dye sols and colored latex are examples of "direct" labels.

Recently, a technology combining binding assay methods and porous carrier materials has been developed. One component of the binding pair (for example, antibody or antigen), is immobilized onto the porous carrier material (for example, a fibrous or porous membrane) by one of the many methods well known in the art, for instance by absorption or covalent linking.

For example, in a competition assay, a sample containing analyte is typically mixed with a labeled analyte or labeled analyte analog (the reagent) capable of specifically binding with the immobilized component. The mixture is then applied to the porous carrier material. Migration of the mixture, caused by capillary wicking within the porous carrier material, brings the reagent to a position where it competes for a limited number of binding sites of the immobilized specific binding component. A portion of the labeled reagent specifically binds to the immobilized reagent and in turn becomes immobilized. The amount of bound labeled reagent is in inverse proportion to the amount of analyte in the sample.

Excess, unreacted material is removed by washing, for example by applying appropriate volume of an eluant to the porous carrier material. After washing, the label can be developed and/or measured ("indirect" label), or visually evaluated ("direct" label). 5 Labeled reagent can also be impregnated into the porous carrier material so that the labeled reagent becomes mobile when moistened. In such a case, the addition of the sample itself may be sufficient to initiate and run the assay.

Deutsch, et al. (U.S. Pat. Nos. 4,094,647, 4,235,601 and 4,361,537, the contents of which are herein incorporated by reference) discloses a test device for determining a characteristic of a sample (a specific binding assay) in which reagents are mixed and transported in a transportative strip element (also see Baker, et al., WO 87/02774, published May 7, 1987). In one embodiment, a first specific radiolabeled reagent is impregnated into the strip, and a second reagent is immobilized onto the strip downstream of the first reagent via attachment to microbeads. A sample is applied upstream of the first reagent, and the beginning end of the strip is dipped into an eluant. Eluant migrating through the strip picks up the sample. The eluant containing the sample then rehydrates the first reagent, mixes it with the sample, and transports the sample and first reagent to the second reagent, where a specific binding reaction immobilizes a portion of the radiolabeled reagent. Excess radiolabeled reagent is washed away towards the terminal end of the strip. Alternatively, labeled reagent may be applied directly to the strip body.

U.S. Pat. No. 4,938,927 issued to Kelton, et al. (the contents of which are herein incorporated by reference) discloses a rotary fluid manipulator containing a circular chromatographic membrane divided by fluid blocking means into many fluid passages. Each fluid passage contains a labeled specific binding reagent and an immobilized specific binding reagent. A test specimen is applied onto or nearby the labeled reagent. Then, an eluant is applied at a special location close to the center of the membrane. The eluant moves within particular passage towards the outer side of the circle by wicking and centrifugal force. The principles of the specific binding assay itself are identical to those described in Deutsch, et al.

U.S. Pat. No. 5,238,652 to Sun, et al. (the contents of which are herein incorporated by reference) relates to an analytical test device for a competition assay for particular non-protein antigens, such as antigens representing drugs of abuse. Colored latex particles sensitized with detecting antibodies for the non-protein antigen are applied directly to the chromatographic membrane in such a way that latex spheres are immobile when dry and mobile when contacted with liquid. Downstream of the latex, the membrane is impregnated with a permanently immobile drug conjugate probe. When a sample such as body fluid is applied to the membrane, the latex particles are resuspended by the sample and migrate towards the conjugate. If drugs or their metabolites are present in the sample, binding to antibody on the latex will occur during this migration. If the amount of drug or drug metabolite is sufficient to exhaust all antibody binding sites, binding of the colored latex particles to the drug conjugate probe will be prevented. If there are no drugs or drug metabolites in the sample, then colored latex particles will bind to drug conjugate producing a distinct colored band.

United Kingdom Patent No. 0 291 194 B1, to May, et al., discloses an analytical test device comprising a hollow casing containing a chromatographic porous membrane. The device also contains labeled (for example, colored latex) specific binding reagent for an analyte, and an unlabeled specific reagent for the same analyte, permanently immobilized on the membrane. The liquid sample permeates the membrane by capillary action, picking up the labeled reagent and migrating to the zone with the unlabeled specific reagent. The presence of an analyte within the sample is determined by the extent of labeled reagent binding using either a sandwich or a competition format.

To minimize undesirable interactions between the labeled reagent and the membrane, which may cause irreversible sticking of the labeled reagent to the membrane, it was suggested to apply the labeled reagent as a surface layer. To achieve this, a glazing material, such as aqueous sucrose or cellulose, is applied prior to the application of the labeled reagent to form a glaze layer. The labeled reagent is then applied on top of the glaze. In practice, however, the glazing material penetrates to some extent into the thickness of the membrane, as does the labeled reagent.

U.S. Pat. No. 5,275,785, to May, et al., ("May '785", the contents of which are herein incorporated by reference) discloses a chromatographic test device incorporating multiple liquid conductive membranes of different wicking ability and a liquid-swellable "switch" material to regulate liquid flow. Different liquid migration speeds in the separate membranes in combination with the liquid-swellable "switch" material (which establishes or breaks contact between the membranes) allow for delivery of reagents to the detection zone in a certain order and/or proportion.

Unfortunately, the known technologies referred to above, suffer numerous disadvantages. Two problems of particular concern deal with mobilizing dry binding reagents: the first relates to quantity of reagents mobilized, the second to the fashion of mobilization. Although a goal is to mobilize reagents quantitatively, this is often not possible in practice because reagents tend to irreversibly stick to the porous material.

It is preferred to uniformly mobilize reagents to form a continuum with no or minimal concentration gradient. Such a continuum favors a uniform degree of binding (especially critical for the competition assays), and prepossesses a reproducible uniform result band. One known way to achieve mobilization and a uniform concentration throughout solution of the reagents is to premix a sample and a liquid binding reagent, for instance labeled binding reagent, and then apply the mixture to a test device, either directly or via a mediating sample pad. Regrettably, however, this multistep procedure is predisposed to experimental error and increases handling of potentially hazardous samples.

Another problem associated with certain analytes relates to the speed of migration/ability to migrate within the absorbant material. This has particularly been found to be true for hydrophobic analytes, such as cannabinoids and benzodiazepines. To overcome this problem, the subject invention provides for the use of cyclodextrins.

Cyclodextrins are cyclic oligosaccharides having at least six glucopyranose units. Natural, commercially available cyclodextrins are α-, β- and γ-, having 6, 7, and 8 glucopyranose units, respectively. Topographically, cyclodextrins are shaped as a torus. Their outer surface is hydrophilic, making them soluble in water; their inner cavity is hydrophobic. Accordingly, cyclodextrins are capable of forming inclusion complexes with hydrophobic guest molecules of suitable diameters.

The most important characteristic from the standpoint of ability to encapsulate guest molecules, and hence change the guest molecule's physicochemical properties, is the internal diameter of the cyclodextrin's cavity and its water solubility. Internal diameter increases from α- to β- to γ-cyclodextrin: approximately 5, 6 and 7.5 angstroms, respectively. A large number of cyclodextrin derivatives, the majority of which are highly water-soluble, have been prepared and are described in the literature (see for example Croft, A. P. and R. A. Bartsch, *Tetrahedron,* 39(9):1417–1474 (1983)).

Industrial applications of cyclodextrins are numerous and span many industries. Applications include improvement of chemical stability, for instance drug and vitamin stability, enhancement of hydrophobic molecule solubility, enhancement of drug bioavailability, elimination or reduction of undesirable tastes and/or odors, transformation of liquid into solid, defoaming, and use in chemical separations (for reviews see Duchene, D. and D. Wouessidjewe, *J. Coord. Chem.,* 27:223–236 (1992), J. Szejtli, In: Inclusion Compounds, V.3, Ed. J. L. Atwood, et al., Academic Press, 1984, pp. 331–390).

Japan Patent Publication No. 05196623 in the name of Kureha Chem Ind Co. Ltd., discloses a test slide for diagnosing a minor substance in body fluid. A reagent containing latex particles sensitized with immune reactive substance is dried onto the surface of a slide in the presence of polyvinylpyrrolidone and cyclodextrin so that the reagent layer is not sticky, and has good redissolution characteristics and stability.

Applications of cyclodextrins and cyclodextrin polymers in chromatography are extensive, for example in thin layer, gas-liquid, high performance liquid (HPLC), affinity, and electrokinetic chromatography (for reviews see; Sybilska, D. and E. Smolkova-Keulemansova, In: Inclusion Compounds, V. 3, Ed. J. L. Atwood, et al., Academic Press, 1984, pp. 173–243; Szejtli, J., et al., In: Ordered Media in Chemical Separations, Ed. W. L. Hinze, D. W. Armstrong, ACS Symposium Series 342, American Chemical Society, Washington, D.C., 1987, pp. 200–217).

Cyclodextrins and cyclodextrin polymers can be used as stationary phase and/or mobile phase components. The ability of cyclodextrin to selectively bind apolar molecules, or portions of such molecules whose shape and dimensions correspond to those of the cyclodextrin cavity, can be utilized under conditions where a discrete amount of cyclodextrin or cyclodextrin polymer is added to an aqueous mobile phase. When an inclusion complex is formed, the hydrophobic portion of the guest molecule is either partially or fully included in the cyclodextrin cavity and is therefore no longer available for direct interaction with the stationary phase. Instead, the hydrophilic outer surface of cyclodextrin presents itself to the stationary phase, typically reducing absorption of the inclusion complex relative to the absorbtion of the corresponding free guest molecule.

The use of an α-cyclodextrin mobile phase in thin-layer chromatographic separations of substituted phenols using aqueous α-cyclodextrin mobile phase and polyamide stationary phase has been described (Burkert, W. G., et al., *J. Liquid Chromatogr.,* 44:1065–1085 (1981)). Without cyclodextrin, the Rf value (the ratio of the distance traveled by a compound to that by the solvent front) was low and undiscriminating for the isomers. In the presence of cyclodextrin, migration improves and Rf increases, apparently due to cyclodextrin complex formation.

Likewise, the effect of β-cyclodextrin on lipophilicity of antibiotic polymyxine has been examined using standard and reverse-phase thin-layer chromatography (Cserhati, T., et al., *J. Chromatogr.,* 259:105–107 (1983), also see *J. Inclusion Phenomena,* 1:53–59 (1983), Ibid., 1:395–402, (1983/1984), Ibid ., 4:55–59, (1986)). β-cyclodextrin forms inclusion complexes with polymyxine, reducing its lipophilicity and its adsorption energy to silica gel and cellulose, and significantly increases the Rf value.

Cyclodextrin as mobile-phase components for separation of isomers by reverse-phase HPLC has been described (D. Sybilska, In: Ordered Media in Chemical Separations, Ed. W. L. Hinze, D. W. Armstrong, ACS Symposium Series 342, American Chemical Society, Washington D.C., 1987, pp. 218–234). For all studied compounds, apparent capacity factor decreased with the increase in β-cyclodextrin concentration, suggesting that adsorption of cyclodextrin complexes on RP-18 phase is always smaller than that of corresponding free guest molecules.

The present invention teaches the use of inclusion compounds, such as cyclodextrins, in binding assays, for example, in the mobile phase of specific binding assays. This constitutes a new application for cyclodextrins. In the subject apparatus and method, it is convenient to spacially separate the location where the sample is deposited from mobile binding component. As a result, analyte containing sample travels through a sample pad, and/or some distance through the membrane, before the mobile binding component is mixed with the sample.

As can well be appreciated, during this travel partial or complete loss of analyte may occur due to absorption on the sample pad and membrane. Depending on the type of interaction with the stationary phase materials, analyte may become irreversibly bound or may travel more slowly than the solvent front. Such chromatographic retention is undesirable because of sensitivity loss and lack of reproducibility due to variations in the matrix and metabolite composition of the samples. In a worst case scenario, analyte could become strongly absorbed by stationary phases and therefore migrate very slowly. In such a case, liquid front may contain no analyte and the test will give a negative result. It is therefore an object of the subject invention to eliminate or reduce this undesirable phenomenon.

One-step devices require only the single step of adding sample to perform a test. The binding reagent is usually embedded into an absorbant material which is in serial contact with the porous carrier material or directly applied to the porous carrier material. However, in such cases the liquid front of a sample non-uniformly mobilizes the dry impregnated binding reagent so that the reagent concentration is highest at the front, thus resulting in a non-uniform concentration pattern which is very sensitive to any variation in the porous carrier material. Even small lot-to-lot differences can cause an adverse affect and precise titration of the labeled reagent is required. Since the titer is chosen with respect to performance at cutoff level of an analyte, it is often difficult to achieve substantial differentiation between no analyte and analyte-at-cutoff signals.

Other disadvantages of known one-step systems are non-uniform migration of labeled binding reagent and poor rehydration of latex. The prior art attempted to overcome the problem of poor rehydration and irreversible sticking of latex by applying a binding reagent to the surface layer on top of glazing material (see for example, May, et al., discussed above). However, the viscous compounds which form the glazing material deteriorate migration and cause eddies. This leads to poor reproducibility and a broken result band. In a competitive format, the disadvantages are more acute than in a sandwich assay format.

The subject invention overcomes the above-mentioned problems and provides an improved specific binding assay through the use of an additional top membrane (a porous carrier material) which contains a specific binding reagent. Through an additional independent membrane impregnated with specific binding reagent, rehydration of the specific reagent and the extent of its dilution by the sample is controlled thereby optimizing the performance of the assay. This unique design achieves a more uniform migration pattern of the labeled reagent, and eliminates undesirable flooding of the membrane body when excessive sample volume is applied.

The subject invention can be used with, but is not limited to, the Roche "ONTRAK-TESTCUP®" for conducting specific binding assays, in particular drug of abuse assays. The cup is configured and dimensioned to incorporate the porous carrier material test strips. "ONTRAK-TESTCUP®" is disclosed in the co-owned pending U.S. patent application Ser. No. 08/122,227, filed Sep. 16, 1993, the contents of which are hereby incorporated by reference.

SUMMARY OF THE INVENTION

The present invention relates to apparatuses and methods utilizing porous carrier materials transport of reagents and sample to perform specific binding assays.

The subject invention provides an apparatus for conducting a binding assay. The apparatus comprises a first and a second absorbant material. The first absorbant material has a first reagent immobilized thereon at a first predetermined location. The second absorbant material is in contact with the first absorbant material and has a second reagent releasably immobilized thereon at a second predetermined location. The first absorbant material and the second absorbant material are positioned in juxtaposition to each other so that a flow of liquid through the first absorbant material causes the second reagent to be released from the second absorbant material and flow through the first absorbant material.

The subject invention also provides a method for conducting a specific binding assay. This method can be dissected into four phases. The first phase involves introducing a liquid sample into a first absorbant material to generate a first flow of liquid within the first absorbant material. The second phase involves introducing the liquid from the first absorbant material into a second absorbant material to generate a second flow of liquid within the second absorbant material while maintaining the first flow of liquid within the first absorbant material. The third phase involves introducing a second reagent into the second flow of liquid within the second absorbant material. The second flow, after the introduction of the second reagent, is in a direction generally parallel to the first flow of liquid within the first absorbant material. And, the fourth phase involves introducing the second flow of liquid and the second reagent from the second absorbant material into the first absorbant material to unite with the first flow of liquid within the first absorbant material.

DETAILED DESCRIPTION

Figure 1A:
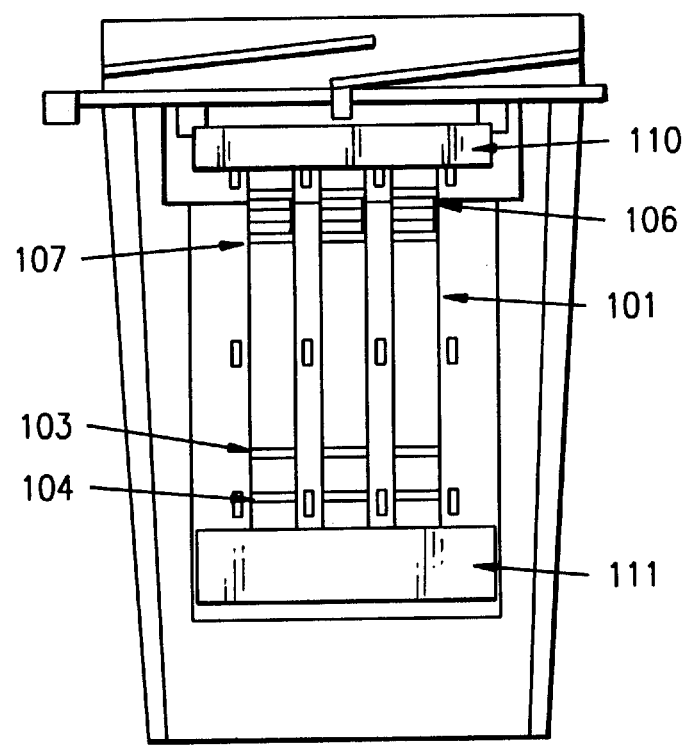
FIG. 1A depicts a front view of the strip compartment of the "ONTRAK TESTCUP® modified to contain the subject apparatus," without cover panel.
Figure 1B:
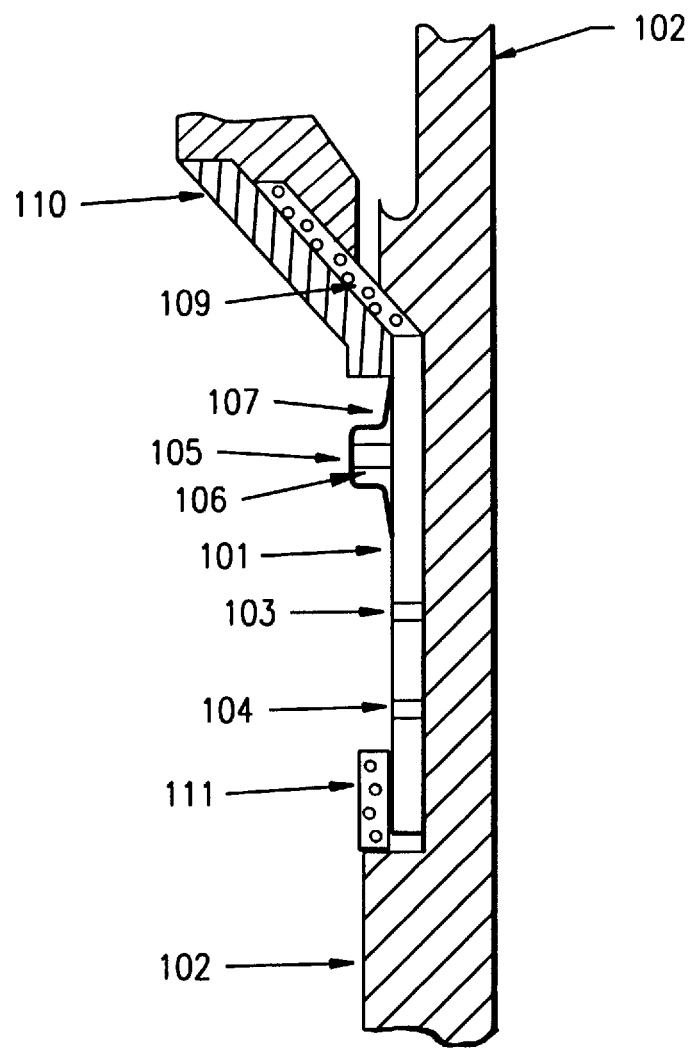
FIG. 1B depicts a side section view of FIG.1A

The subject invention is described below in terms of its preferred embodiments. These embodiments are set forth to aid in understanding the invention, but are not to be construed as limiting.

The apparatus and method of the present invention are particularly well suited for use in testing drugs of abuse, such as cocaine, amphetamines, cannabinoids, barbiturates, benzodiazepines, opiates, phencyclidines, propoxyphine, methaqualone, tricyclic antidepressants and methadone, as well as for clinical chemistry, pregnancy, and similar testing.

As used throughout the specification, the terms "membrane," "porous carrier material" and "absorbant material" have been used interchangeably, and are to connote a material suitable for the assays described herein.

To aid in understanding the invention, several positional terms have been used. The "top" and "main" membranes have been described with the terms "forward" and "rearward." "Forward" is the portion of a membrane which extends beyond the lengthwise midpoint (located in the direction of liquid flow within the membrane). The most forward portion of a membrane is referred to as the "terminal end." "Rearward" is opposite of forward and relates to the portion of the membrane which precedes the lengthwise midpoint in the direction of the end initially contacted by the liquid sample. The most rearward portion of the membrane is referred to as the "beginning end." "Downstream" is the direction in which the liquid flows within the membranes. In contrast, "upstream" relates to a direction opposite the flow of liquid within the membrane.

A sample is absorbed at the beginning end of the main membrane and is transported along the length of the main membrane by capillary action. Generally, membrane length is in the range of 1–10 cm, width 0.4–2 cm, and thickness 0.1–1 mm.

Typically, the membrane is shaped as an elongated, thin rectangular prism.

When the sample flow reaches the reagent-containing top membrane (generally containing a labeled reagent), it splits into two flows: one continues to run in the main membrane, the second permeates into the top membrane, typically in the rearward portion, and mobilizes the reagent located within the top membrane. The reagent within the top membrane is mobile when in a moist state. Although for clarity a single reagent is described as being in the top membrane, it should be appreciated that multiple reagents may also be employed. Likewise, a plurality of top membranes each containing one or more reagents may be utilized.

Preferred labels are colored colloidal particles, and colored latex is most preferred. Colored latex is readily visible to the naked eye when bound in the detection zone, therefore no additional developing procedures are required. Procedures for sensitization of latex with specific binding reagents are well known in the art (for example, see Illum, L. and P. D. E. Jones, Attachment of Monoclonal Antibodies to Microspheres, *Meth. Enzymol.*, 112:67–84 (1985)) and Galloway, R. J., Development of Microparticle Tests and Immunoassays, *Seradyn*, pp. 6–31 (1988)). As alluded to above, multiple reagents may be utilized in one or more top membranes. As such, multiple latex containing membranes or one latex containing membrane sensitized with a plurality of binding reagents, for example antigens and/or antibodies, may be employed.

The two parallel flows reunite and mix in the main membrane near or at the forward edge of the top membrane. While migration continues towards the detection site within the main membrane, a binding reaction between the reagent and the analyte takes place. The extent of this binding or simply the presence of the analyte, depending on whether the assay is a competition or a sandwich format, is measured at a detection site, where specific binding with the immobilized reagent occurs. Unbound material continues to migrate downstream towards the terminal end of the main membrane and is partially captured at the control site. No unbound labeled reagent remains in the detection or the control sites.

On the main membrane there is a detection site where specific binding reagent (generally unlabeled) is immobilized (that is, the immobilized specific binding reagent cannot be washed away by a developing liquid). Downstream of the detection site there is a control site, where another binding reagent is immobilized. When assembled, the top membrane is in contact with the upper surface of the main membrane upstream of the detection site (see FIG. 1D).

Optionally, a sample pad can be used to absorb a liquid sample and release the liquid into the beginning end of the main membrane. The sample pad is typically fashioned from a blotting material, and is in contact with the main membrane. The sample pad may optionally contain additional reagents.

Optionally, a "sink" pad, fashioned from a blotting material, can be used at the terminal end of the main membrane to absorb excess reagent solution and foster capillary flow in the main membrane for a longer period of time.

The membranes and the pads are preferably disposed in a holder. The use of a sample pad and a sink pad are described in U.S. Pat. Nos. 4,956,302 and 5,238,652, the contents of which are herein incorporated by reference. A skilled artisan having read the present specification would be able to use such pads in connection with the present invention.

Examples of suitable top and main membranes include bibulous or fibrous material capable of capillary action, such as thin layer chromatography materials, paper or cellulose chromatography substrates, porous synthetic plastics, etc. Preferred absorbant materials have good wicking ability, a smooth surface which insures good contact between the "main" and "top" membranes, reversible binding of the labeled compound to the membrane to promote quantitative mobilization, ability to transport a labeled reagent by capillary action, availability of wicking characteristics within suitable range, reproducible and convenient reagent application and handling.

Preferred membranes include nitrocellulose and nylon. Moreover, membranes precast on plastic are preferred because of handling convenience. Nitrocellulose is desirable because it (i) is able to bind proteins by adsorption without requiring complicated covalent linking, (ii) has excellent wicking characteristics, and (iii) is available in a convenient range of pore sizes. Backed nitrocellulose (for example, precast on a plastic material), is most preferred.

Procedures for adsorption of specific proteins on nitrocellulose to form detection and control sites, and blocking of unoccupied binding sites on the nitrocellulose with neutral blocking reagent are well known in the art (see for example, Harvey, M. A., Optimization of Nitrocellulose Membrane-Based Immunoassays, *Schleicher & Schuell*, No. 557, pp. 18–23, 1991).

Migration rates vary with membrane properties, for example, pore size. Selection of flow rate, appropriate membrane type, and pore size is within the knowledge of the skilled artisan, and can be determined with minimal experimentation.

Because of the fluid dynamics within the top membrane, reagent (typically labeled) tends to concentrate at the forward edge of the top membrane and seep slowly into the main membrane where it mixes with the first flow. The extent of dilution has been postulated to be controlled by flow dynamics in the present invention rather than by the rate of reagent mobilization, as in known formats. Thus, the subject invention provides the advantage of relatively constant concentration of the top membrane reagent within the reunited flow which occurs downstream in the main membrane. This constant concentration of reagent is maintained as long as the reagent supply in the top membrane lasts.

The rate of reagent dilution from the top membrane can be controlled by choosing an appropriate difference in wicking rates between the main membrane and the top membrane. "Wicking rate" refers to the speed of liquid movement within the membrane (distance/time). The top membrane can be made from the same material or other suitable porous carrier material. However, for convenience, the top and the main membranes are generally made from the same material. Such a choice of appropriate membrane materials is readily made by the skilled artisan having read the present specification. For instance, when a higher rate of dilution is required, reagent can be applied via a membrane having slower wicking properties, for example, by using a membrane having a smaller pore size.

The wicking rate for the main membrane is preferably higher than or equal to the wicking rate of the top membrane. As a result, reagent from the top membrane permeates into the main membrane behind the liquid front in the main membrane, thus allowing the first flow to prewet the main membrane. Prewetting advantageously (i) facilitates uniform migration of the reagent from the top membrane, (ii) eliminates or at least significantly reduces negative effect of hydrophobicity due to unlabeled binding reagents at the detection site, and (iii) facilitates binding at the detection site.

A labeled binding reagent is normally applied to a membrane which has previously been blocked with a blocking compound in order to avoid non-specific binding of a labeled reagent to the membrane surface.

The membrane can be cut and the test strips assembled in any suitable manner. Alternatively, the membrane may be pre-formed to certain dimensional specifications. For instance, it can be convenient to assemble large segments first by securing the top membrane on the surface of the main membrane, which is then cut into strips. The top membrane preferably is the same width as the main membrane, or is more narrow. The length of each membrane is determined empirically, but relatively short membranes with the dimensions just sufficient to accommodate the required amount of a binding reagent are preferred. Exact distance between the membrane and the detection site is determined by balancing the time required for proper mixing of the reagents and completion of a binding reaction, with the deterioration of uniform migration if the distance is too long. Such spacial parameters can be determined through minimal experimentation. Presently, a distance in the range from 0.5 cm to 5 cm is preferred. Position of the top membrane on the main membrane is upstream of the detection site, but downstream of the sample application site.

Lamination of the main and top membranes further prevents occasional membrane flooding due to excess sample traveling outside of the membranes. If a flood wave of sample reaches the location where reagent is imbedded, it may completely distort the test result. This problem is particularly acute in the applications where the sample migrates downwards.

Contact between the top and main membranes can be achieved in a number of ways. For instance, the main and the top membranes can be pressed against each other by housing elements, or may be laminated one to another, or both. Lamination is preferred because a reliable "tight" contact is achieved. Moreover, the laminate acts as a dam to prevent flooding. A preferred way to maximize contact between the membranes, involves laminating the top membrane over the main membrane in juxtaposition using mylar, such as the MYLAR® tape described in the following example.

Currently it is preferred for reagent from the top membrane not to cross the interface between the membranes to any appreciable extent, but rather to be transported completely inside the top membrane towards the forward edge.

Figure 1C:
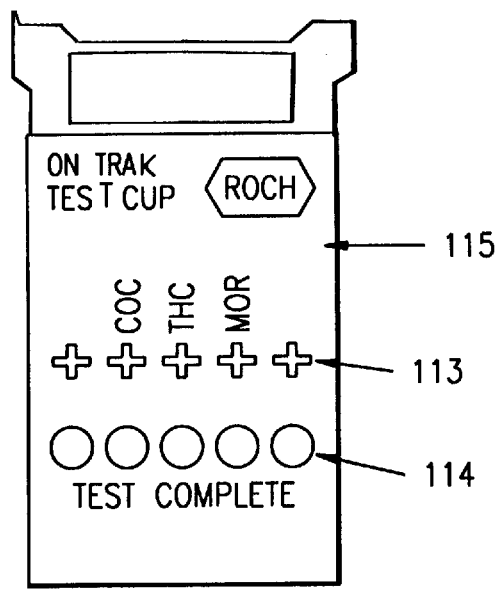
FIG. 1C depicts "ONTRAK-TESTCUP®" cover panel.
Figure 1D:
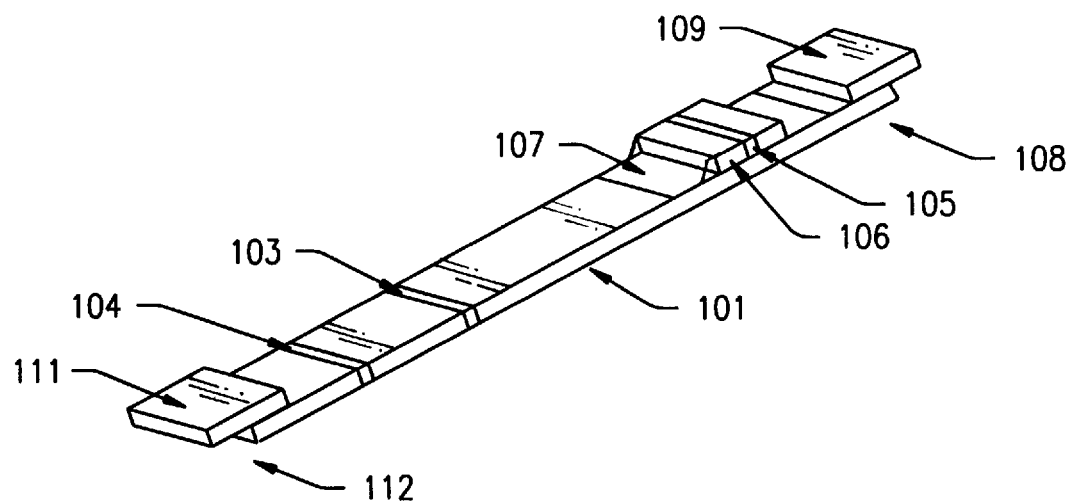
FIG. 1D depicts a perspective view of the test strip according to the present invention.

FIGS. 1A through 1D, depict a specific device which utilizes chromatographic principles to perform specific binding assays. Three porous carrier membranes testing three different analytes are shown in a plastic holder (102). Such a holder may form a portion of the "TESTCUP™" device as described in U.S. patent application Ser. No. 08/122,227, the contents of which are herein incorporated by reference. Typically, plastic holder (102) will retain three to five porous carrier membranes. FIG. 1A shows three porous carrier membranes, whereas FIG. 1C shows windows for five porous carrier membranes.

Main membrane (101) contains detection site (103) and control site (104). Labeled specific binding reagent (105) is embedded in top membrane (106) which contacts the upper surface of main membrane (101). Top membrane (106) is tightly attached to main membrane (101) with adhesive MYLAR tape (107). Contacting, and preferably slightly overlapping, beginning end (108) of each main membrane (101) is sample pad (109). Sample contacts sample pad (109) through several small holes in the back side of the pad (not shown). A soft rubber seal (110) sits on the top of sample pad (109). The degree of softness needed is readily determined by the skilled artisan. Seal (110) is somewhat dimensionally larger than sample pad (109), so that it covers sample pad (109) and seals it along its borders when squeezed.

Sealing is required to prevent leakage of the sample when the chromatographic membranes are installed vertically (sample migrates in a downwards direction). Of course, a seal (110) can also be used when the apparatus is used in other than a vertical position. Absorbant pad (111) at the terminal end (112) of the chromatographic membranes is common to all three membranes. The detection site can be observed through cross-shape result window (113), the control site through the circular control window (114) of the cover panel (115). Plastic of the cover panel is typically not transparent.

The present invention is particularly useful in a competition assay format. In one version of this format, the labeled reagent in the top membrane is either the analyte itself or an analog capable of the same type of specific binding. The labeled reagent is mobilized and diluted by a sample, and migrates with the sample towards the detection site, where unlabeled reagent capable of binding the analyte or its structural analog is immobilized. If analyte is present in a sample, it will compete with the labeled reagent for a limited number of binding sites in the detection zone, and the relative concentration of the analyte can be determined from the extent of reduction of binding of the labeled reagent.

In another version, competition is time resolved. In this case, the labeled reagent is a binding partner of the analyte or of its structural analog. The labeled reagent is mobilized and diluted by a sample, and then migrates with the sample towards the detection site, where the unlabeled analyte or its analog is immobilized. If analyte is present in the sample, then during the course of migration it will bind to the labeled reagent. Remaining unsaturated binding sites of the labeled reagent can bind to the immobilized reagent in the detection site. Once again, concentration of the analyte can be determined from the extent of reduction of binding of the labeled reagent.

For both versions of the competition format, the ratio of concentrations of binding components in migrating liquid should not fluctuate significantly over the dimensions of the labeled reagent moving zone. Also, uniformity should not decay over the term of migration to the detection site. Deviation in flow uniformity allows competition to fluctuate, and leads to poorly reproducible results. The present invention minimizes non-uniformity, and improves sensitivity by making the labeled reagent more dilute (as described below).

Discrimination between zero analyte level and cut-off analyte level can be improved by increasing the total amount of labeled reagent and increasing the volume in which it is presented. As a result, analytical signal at zero drug level becomes stronger, while the signal at cut-off level is kept unchanged, the steeper calibration curve allows better discrimination.

The present invention is also useful in a sandwich format. In this format, both the labeled reagent and the unlabeled immobilized reagent are the binding partners of the analyte (though they typically should bind to different epitopes of the analyte). Preferably both the labeled and immobilized unlabeled reagents are present in excess of the analyte. If analyte is present in the sample, then during the course of migration it will fully bind to the labeled reagent. In the detection site, analyte, which is already bound to the labeled reagent, will bind to the immobilized reagent, forming the sandwich. The analyte concentration is directly proportional to the binding at the detection site.

Because some hydrophobic analytes tend to stick to the sample pad, main and top membranes, causing distortion of test results, inclusion complexes of these hydrophobic analytes may be used to reduce unwanted absorption onto these materials. The term "inclusion complexes" is to include any combination of analyte and an "inclusion compound." The term "inclusion compound" means any compound capable of interacting with an analyte to effect a change in 5 solubility of the analyte within a carrier liquid or the degree of absorbtion to surrounding materials. Although chemicals capable of forming inclusion complexes with analyte can be added directly to the sample, this is not often desirable. A better solution is to incorporate soluble inclusion compounds, such as α-cyclodextrin, β- cyclodextrin, γ-cyclodextrin, other cyclodextrin, their derivatives or cyclodextrin polymers, into the sample pad, and/or main, and/or top membranes. These compounds (in the range of 0.001–1M, preferably 0.01–0.5M) are chosen to form an inclusion complex with analyte of interest, possibly of various molar ratio. For instance, use of cyclodextrin may be beneficial for small drug molecules.

Mobile phase containing inclusion compounds, such as cyclodextrin or others, may be useful for certain hydrophobic haptens. As it was outlined before, formation of an inclusion complex reduces absorption and facilitates migration concomitant with the liquid front. Solutions containing inclusion compounds, such as cyclodextrins, can be dried and thereby incorporated into the sample pad and/or membrane. When sample is applied, the complex will form before migration begins. Absorption of the inclusion complex is normally lower than that of the corresponding free hapten. Thus, migration of an analyte will ideally proceed with or very close to the solvent front, and reagent binding after its rehydration will react with the same concentration of analyte as in the sample.

Inclusion compounds should dissolve easily (at least partially) and rapidly form inclusion complexes to facilitate migration of analyte through the pad and membrane, reducing absorption to these materials. Usually, specific binding reagents, such as for example antibody, have a much higher affinity towards the analyte and will extract the analyte out of the inclusion complexes upon mixing. Thus, the inclusion complex serves a means of transportation while not significantly affecting the specific binding reaction. Such approach has proved successful in case of cannabinoids and benzodiazepines (see Example 2). With these analytes, the use of β-cyclodextrin, its highly soluble derivatives, such as hydroxypropyl-βcyclodextrin, and highly soluble low molecular weight β-cyclodextrin polymers is preferred (for extensive listing of the derivatives see Croft, A. P. and R. A. Bartsch, *Tetrahedron*, 39(9):1417–1474 (1983)).

EXAMPLE 1

The following example of a tetrahydrocannabinoid assay is provided to illustrate the invention. It must be pointed out, however, that the present invention is not limited to any particular substance.

Tetrahydrocannabinoid (THC) derivative—1-[[(6a,7,10,10a-Tetrahydro-1-hydroxy-6,6-dimethyl-3-pentyl-6H-dibenzo [b,d]-pyran-1-yl(carbonyl]oxy]-2,5-pyrrolidinedione—was prepared as described in *J. Org. Chem.*, 51:5463–5465 (1986) and European Patent Application Publication No. 90 104 055.

Conjugation of this THC derivative to bovine serum albumin (BSA) was performed as follows: To 100 mg/ml solution of BSA in 50 mM potassium phosphate at pH 7.5 (2 mL) (cooled in an ice bath), dimethylsulfoxide (DMSO) was added dropwise (1.5 mL), then 10 mg/mL solution of the above mentioned derivative in DMSO (2.5 ml) was added dropwise. The reaction mixture was stirred at room temperature for 16 hours and then transferred to dialysis tubing and dialyzed first against 20 volumes of 30% DMSO—potassium phosphate buffer (50 mM, pH 7.5), second against 10% DMSO—potassium phosphate buffer, and third for four times more against potassium phosphate buffer.

Carboxylate-modified blue latex from Seradyn (0.3 micron particles) was first washed three times at 1% solids by centrifuging in 20 mM, pH 6.1 MES (2-[N-morpholino] ethanesulfonic acid). The washed latex was then adjusted to 5% solids in MES and (i) sensitized with 0.1 mg/mL anti-THC monoclonal antibody for 16 hours at room temperature, (ii) blocked with BSA solution in MES for 1 hour at room temperature, then (iii) washed for three times at 1% solids in MES by centrifugation, and (iv) adjusted again to 5% solids. Before use, equal volumes of this latex and 35% w/v sucrose in PBS were mixed.

Mylar backed large pore size nitrocellulose (10–20 micron) from Millipore was cut into pieces of 10 cm in length and 5 cm in width. Solution of THC-BSA conjugate (about 1 mg/mL) and anti-BSA monoclonal Ab (about 2 mg/mL), both in 50 mM potassium phosphate buffer pH 7.5, were dispensed using IVEK Corp. Digispense 2000™ system at the rate 1 μl/cm onto nitrocellulose at a distance respectively 2 cm and 1 cm from the 10 cm side. Nitrocellulose segments were allowed to dry for about 30 min. at 37° C. and then were blocked with 1% w/v polyvinyl alcohol (PVA, m.w. 13,000–23,000) solution in 20 mM Tris pH 7.4 for 30 min. at room temperature. The segments were then rinsed in water and dried.

Sample pads were prepared by soaking BioRad gel blotter in 0.1 mol/L potassium phosphate buffer pH 7.5 containing 30 mg/ml β-cyclodextrin, drying it and cutting into 1 cm² pieces. The same untreated Biorad gel blotter was used for the sink pads.

The same nitrocellulose as described above in this example was used as a separate membrane for latex (top membrane). For this purpose the nitrocellulose, which was previously blocked in the same manner as the main membrane, was cut into 5 mm wide strips and latex was applied using IVEK dispensing system. After drying for 30 min. at 37° C., this membrane was placed nitrocellulose surface down onto the main membrane and laminated to the main membrane with Adhesive Research Inc. adhesive mylar. After this, the segment was cut into 5 mm wide strips, sample and sink pad placed respectively at the beginning and terminal ends of the strips, and the calibration curve obtained using solutions containing predetermined amount of the drug metabolite (11-nor-Δ9-THC-9-COOH).

Figure 2:
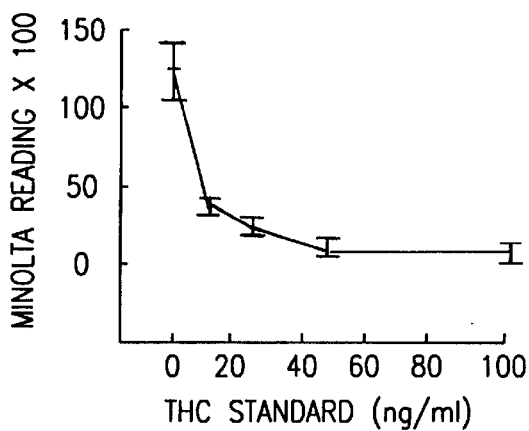
FIG. 2 Graph of calorimetric density vs. THC concentration for an assay conducted using the apparatus of the present invention.

The optimal calibration curve (3.0 μl/cm of latex) is shown in FIG. 2. This, and the following curves, were obtained by determining the colorimetric density of the result bands using Minolta CR-241 Chroma Meter. For each strip colorimetric density in the red part of spectrum ($D_x$) was measured at five points on the conjugate (or result) band, each point 1 mm apart from the neighboring one. Background colorimetric density level was measured off the result band. Average reading, standard deviation and %CV were calculated.

Figure 3:
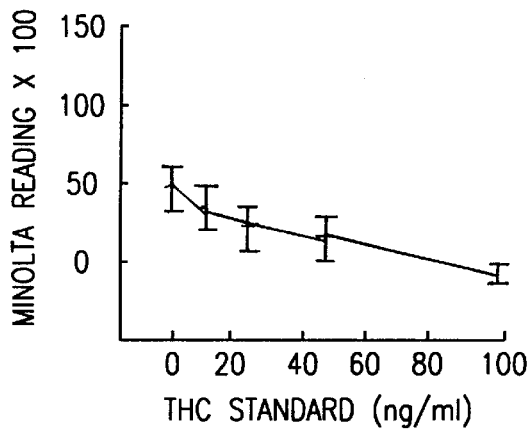
FIG. 3 Graph of colorimetric density vs. THC concentration for an assay conducted using a nitrocellulose onto which reagents had been dispensed using an IVEK Digispense 2000™ system.
Figure 4:
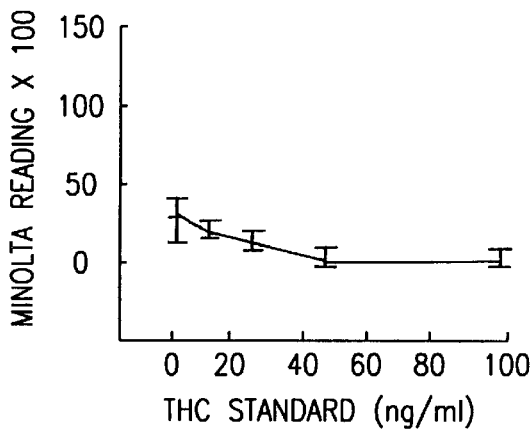
FIG. 4 Graph of calorimetric density vs. THC concentration for an assay conducted using a nitrocellulose onto which reagents had been sprayed using a Paasche airbrush.

For comparison, latex was applied directly to the main membrane. Optimal calibration curves for IVEK dispensing system and for Paasche Company airbrush (1.0 μl/cm of latex for both cases) are shown in FIG. 3 and FIG. 4 respectively. When latex volume larger than 1.0 μl/cm was deposited onto the membrane, inhibition at cut-off concentration (50 ng/ml) was poor.

Figure 5:
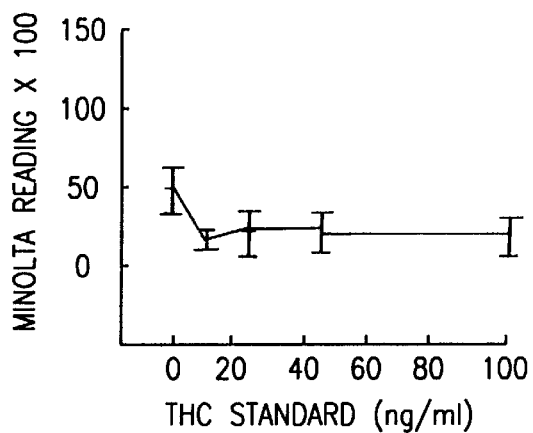
FIG. 5 Graph of colorimetric density vs. THC concentration for an assay conducted on nitrocellulose that had been sucrose glazed.
Figure 6:
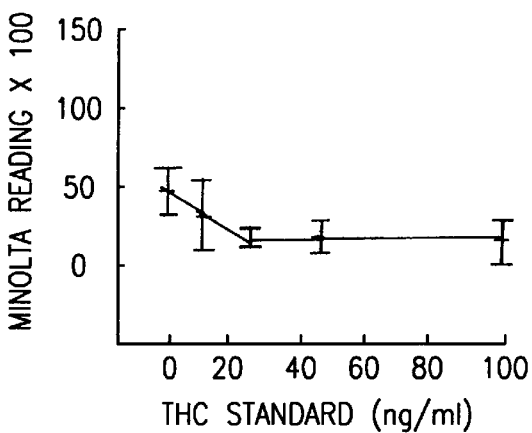
FIG. 6 Graph of calorimetric density vs. THC concentration for an assay conducted using a glazed nitrocellulose with latex in methyl cellulose solution applied over the sucrose glaze.

Performance of the format, where latex is deposited over the sublayer of sucrose glaze (35% to 66% w/v sucrose in water) was also evaluated. An optimal curve with 60% sucrose sublayer and 2.0 μl/cm latex is presented in FIG. 5. A different latex formulation, where latex solution was pre par ed in 1% Methocel K4M™ methylcellulose (Dow Chemical Company) and 0.6% w/v PVA and applied directly on top of the sucrose sublayer, as was suggested in EP 0291194B1, was also evaluated (FIG. 6).

More than half of the latex does not even begin to migrate in this case. The sucrose sublayer also slows migration of latex strongly and migration is not uniform.

Uniformity of the result band and control band can be characterized by color intensity variation for the five reading points. Table 1 presents %CV in control and result band intensities.

TABLE 1

Variation (% CV) in result and control band intensity

| Fig. No. | THC standard concentration | | | Control anti-BSA |
|---|---|---|---|---|
| | 0 ng/mL | 12.5 ng/ml | 25 ng/mL | |
| 1 | 15.5 | 7.9 | 12.5 | 5.3 |
| 2 | 21.4 | 33.1 | 37.2 | 22.7 |
| 3 | 40.8 | 21.5 | 52.7 | 44.3 |
| 4 | 31.8 | 31.2 | 54.8 | 66.0 |
| 5 | 21.6 | 86.6 | 22.9 | 22.6 |

As is clear from the above results, the present apparatus offers results when compared with the systems of the prior art.

EXAMPLE 2

Reagents, materials and assay procedure were the same as in Example 1, except the sample pads were prepared without βcyclodextrin in the buffer solution. In the absence of β-cyclodextrin, no inhibition was observed at the test level of THC in urine. That is, all results were negative.

Upon reading the present specification, numerous alternative embodiments will become obvious to the skilled artisan. These variations are to be considered within the scope and spirit of the invention which is only to be limited by the claims which follow and their equivalents.

What is claimed is:

1. An apparatus for conducting a binding assay, which comprises:
    (a) a main membrane formed from an absorbant material and having a first reagent immobilized thereon at a first predetermined location, the first reagent having an affinity to find with an analyte or a second labeled reagent, the main membrane having a beginning end located at the most rearward position on the main membrane and a terminal end located at the most forward position on the main membrane with the first predetermined location being located between the beginning end and the terminal end; and
    (b) a top membrane formed from an absorbant material, the top membrane being configured, dimensioned and positioned so that it contacts the main membrane at a position forward of the beginning end of the main membrane and rearward of the first predetermined position on the main membrane, the top membrane having the second labeled reagent releasably immobilized thereon at a second predetermined location, the second labeled reagent having an affinity to bind with the analyte or the first reagent, the main membrane and the top membrane being positioned so that a sample introduced at the beginning end of the main membrane would split into two flows, the first flow continuing to flow in a direction from the beginning end toward the terminal end of the main membrane and the second flow flowing parallel to the first flow through the top membrane to cause the second labeled reagent to be released into the second flow, the second flow containing the second labeled reagent then reentering the main membrane and reuniting with the first flow so that the combined flow containing the second labeled reagent flows toward the first reagent immobilized at the first predetermined location.

2. The apparatus of claim 1, wherein the main membrane and top membrane are composed of the same material.

3. The apparatus of claim 1, wherein the main membrane is formed from an absorbant material selected from the group consisting of bibulous membranes and porous membranes.

4. The apparatus of claim 1, wherein the top membrane is formed from an absorbant material selected from the group consisting of bibulous membranes and porous membranes.

5. The apparatus of claim 3, wherein the absorbant material is nitrocellulose.

6. The apparatus of claim 4, wherein the absorbant material is nitrocellulose.

7. The apparatus of claim 1, wherein the main membrane and top membrane are held in contact with each other by a holder.

8. The apparatus of claim 1, wherein the main membrane and top membrane are held in contact with each other by a band of material.

9. The apparatus of claim 8, wherein the material is a polyester film.

10. The apparatus of claim 1, wherein the main membrane has a plurality of reagents immobilized thereon.

11. The apparatus of claim 1, wherein the top membrane has a plurality of labeled reagents immobilized thereon.

12. The apparatus of claim 1, wherein the label is colored latex.

13. The apparatus of claim 1, wherein the both the main membrane absorbent material and the top membrane absorbant material have wicking rates, and the wicking rate of the main membrane absorbant material is the same or higher than the wicking rate of the top membrane absorbant material.

14. The apparatus of claim 1, wherein both the main membrane absorbant material and the top membrane absorbant material have wicking rates, and the wicking rate of the main membrane absorbant material is lower than the wicking rate of the top membrane absorbant material.

15. The apparatus of claim 1, wherein the main membrane and the top membrane have planar surfaces.

16. The apparatus of claim 15, wherein the planar surface of the main membrane is juxtaposed to the planar surface of the top membrane.

17. A method for conducting a binding assay for detection of analytes in a sample within an apparatus containing a main membrane formed from an absorbant material and having a first reagent immobilized thereon at a first predetermined location, the first reagent having an affinity to bind with an analyte or a second labeled reagent, the main membrane having a beginning end located at the most rearward position on the main membrane and a terminal end located at the most forward position on the main membrane with the first predetermined location being located between the beginning end and the terminal end, and a top membrane formed from an absorbant material, the top membrane being configured, dimensioned and positioned so that it contacts the main membrane at a position forward of the beginning end of the main membrane and rearward of the first predetermined position on the main membrane, the top membrane having the second labeled reagent releasably immobilized thereon at a second predetermined location, the second labeled reagent having an affinity for the analyte or the first reagent, which comprises:

(a) introducing a liquid sample into the main membrane to generate a first flow of the liquid sample within the main membrane;

(b) introducing the liquid sample from the main membrane into the top membrane to generate a second flow of the liquid sample within the top membrane while maintaining the first flow of the liquid sample within the main membrane, the first flow of the liquid sample and the second flow of the liquid sample being parallel;

(c) releasing the second labeled reagent from the top membrane into the second flow of the liquid sample within the top membrane; and (d) introducing the second flow of the liquid sample and the second labeled reagent from the top membrane into the main membrane to unite with the first flow of the liquid sample within the main membrane so that the united flow of the liquid sample flows within the main membrane to the first reagent, (e) detecting the presence or absence of the second labeled reagent at the first predetermined location thereby determining whether binding of analytes has occurred.

18. The method of claim 17, wherein the first flow of the liquid sample within the main membrane flows at the same or greater velocity than the second flow of the liquid sample within the top membrane.

19. The method of claim 17, wherein the first flow of the liquid sample within the main membrane flows at a lesser velocity than the second flow of the liquid sample within the top membrane.

* * * * *

UNITED STATES PATENT AND TRADEMARK OFFICE
CERTIFICATE OF CORRECTION

PATENT NO. : 5,770,458
DATED : June 23, 1998
INVENTOR(S) : Alexei Dmitri Klimov and Shiow-Chuan Jane Tsai It is certified that error appears in the above-identified patent and that said Letters Patent is hereby corrected as shown below:

In claim 13, column 15, line 26, please delete "wherein the both the" and replace with -- wherein both the --.

Please delete claim 17 and replace with the following:

-- 17. A method for conducting a binding assay for detection of an analyte in a sample within an apparatus containing a main membrane formed from an absorbant material and having a first reagent immobilized thereon at a first predetermined location, the first reagent having an affinity to bind with the analyte or a second labeled reagent, the main membrane having a beginning end located at the most rearward position on the main membrane and a terminal end located at the most forward position on the main membrane with the first predetermined location being located between the beginning end and the terminal end, and a top membrane formed from an absorbant material, the top membrane being configured, dimensioned and positioned so that it contacts the main membrane at a position forward of the beginning end of the main membrane and rearward of the first predetermined position on the main membrane, the top membrane having the second labeled reagent releasably immobilized thereon at a second predetermined location, the second labeled reagent having an affinity for the analyte or the first reagent, which comprises:

UNITED STATES PATENT AND TRADEMARK OFFICE
CERTIFICATE OF CORRECTION

| | | |
|---|---|---|
| PATENT NO. : | 5,770,458 | Page 2 of 3 |
| DATED : | June 23, 1998 | |
| INVENTOR(S) : | Alexei Dmitri Klimov and Shiow-Chuan Jane Tsai | |

It is certified that error appears in the above-identified patent and that said Letters Patent is hereby corrected as shown below:

(a) introducing a liquid sample into the main membrane to generate a first flow of the liquid sample within the main membrane;

(b) introducing the liquid sample from the main membrane into the top membrane to generate a second flow of the liquid sample within the top membrane while maintaining the first flow of the liquid sample within the main membrane, the first flow of the liquid sample and the second flow of the liquid sample being parallel;

(c) releasing the second labeled reagent from the top membrane into the second flow of the liquid sample within the top membrane; and

UNITED STATES PATENT AND TRADEMARK OFFICE
CERTIFICATE OF CORRECTION

PATENT NO. : 5,770,458
DATED : June 23, 1998
INVENTOR(S) : Alexei Dmitri Klimov and Shiow-Chuan Jane Tsai It is certified that error appears in the above-identified patent and that said Letters Patent is hereby corrected as shown below:

(d) introducing the second flow of the liquid sample and the second labeled reagent from the top membrane into the main membrane to unite with the first flow of the liquid sample within the main membrane so that the united flow of the liquid sample flows within the main membrane to the first reagent;

(e) detecting the presence or absence of the second labeled reagent at the first predetermined location thereby determining whether binding of the analyte has occurred and whether the analyte has been detected. --

Signed and Sealed this

Third Day of August, 1999

Attest:

Q. TODD DICKINSON

Attesting Officer

Acting Commissioner of Patents and Trademarks